(12) United States Patent
Van Bommel et al.

(10) Patent No.: US 12,078,335 B2
(45) Date of Patent: Sep. 3, 2024

(54) LIGHTING ARRANGEMENT FOR ILLUMINATION AND DISINFECTION LIGHTING

(71) Applicant: SIGNIFY HOLDING B.V., Eindhoven (NL)

(72) Inventors: Ties Van Bommel, Horst (NL); Robert Jacob Pet, Waalre (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/271,885

(22) PCT Filed: Jan. 10, 2022

(86) PCT No.: PCT/EP2022/050311
§ 371 (c)(1),
(2) Date: Jul. 12, 2023

(87) PCT Pub. No.: WO2022/152641
PCT Pub. Date: Jul. 21, 2022

(65) Prior Publication Data
US 2024/0077198 A1 Mar. 7, 2024

(30) Foreign Application Priority Data
Jan. 12, 2021 (EP) ..................................... 21151115

(51) Int. Cl.
*F21V 33/00* (2006.01)
*A61L 2/10* (2006.01)
(Continued)

(52) U.S. Cl.
CPC ............ *F21V 33/0064* (2013.01); *A61L 2/10* (2013.01); *F21V 7/0008* (2013.01);
(Continued)

(58) Field of Classification Search
CPC ...... A61L 2/0047; A61L 2/10; A61L 2202/14; F21V 33/0064; F21V 7/0008
See application file for complete search history.

(56) References Cited

U.S. PATENT DOCUMENTS

| 10,413,626 B1 | 9/2019 | Barron et al. | |
| 2015/0247623 A1* | 9/2015 | Hikmet | F21V 7/04 362/84 |

(Continued)

FOREIGN PATENT DOCUMENTS

| CA | 3057913 A1 | 5/2020 |
| EP | 3336417 A1 | 6/2018 |
| GB | 2583881 A | 11/2020 |

*Primary Examiner* — Karabi Guharay

(57) ABSTRACT

A lighting arrangement (100), comprising a first solid state light source (110) arranged to emit visible light, a second solid state light source (130) arranged to emit second light of at least one of violet light and ultraviolet (UV) light, a reflector (140) comprising at least one light-reflecting surface (145), wherein the reflector at least partially encloses the first and second solid state light sources, and wherein at least part of the reflector defines a mixing chamber (150) for mixing the visible light and the second light, a light exit window (160), wherein the visible light and the second light mixed by the mixing chamber are arranged to exit the lighting arrangement through the light exit window, and a third solid state light source (170) arranged to emit UV light, wherein the third solid state light source is arranged outside the mixing chamber.

14 Claims, 3 Drawing Sheets

(51) Int. Cl.
  *F21V 7/00* (2006.01)
  *F21Y 113/00* (2016.01)
  *F21Y 113/13* (2016.01)
  *F21Y 115/10* (2016.01)

(52) U.S. Cl.
  CPC ........ *A61L 2202/11* (2013.01); *A61L 2202/14* (2013.01); *F21Y 2113/13* (2016.08); *F21Y 2113/30* (2023.05); *F21Y 2115/10* (2016.08)

(56) References Cited

U.S. PATENT DOCUMENTS

| | | |
|---|---|---|
| 2018/0172219 A1 | 6/2018 | Van Bommel et al. |
| 2018/0180226 A1 | 6/2018 | Van Bommel et al. |
| 2018/0318599 A1 | 11/2018 | Van Bommel et al. |

\* cited by examiner

LIGHTING ARRANGEMENT FOR ILLUMINATION AND DISINFECTION LIGHTING

CROSS-REFERENCE TO PRIOR APPLICATIONS

This application is the U.S. National Phase application under 35 U.S.C. § 371 of International Application No. PCT/EP2022/050311, filed on Jan. 10, 2022, which claims the benefit of European Patent Application No. 21151115.9, filed on Jan. 12, 2021. These applications are hereby incorporated by reference herein.

FIELD OF THE INVENTION

The present invention generally relates to lighting arrangements. More specifically, the lighting arrangement is arranged to provide a combination of a desired illumination and a disinfection (bactericidal) lighting effect.

BACKGROUND OF THE INVENTION

Disinfection lighting has become a topic of renewed interest as the demand for sterilization increases. For example, the use of deep UV (ultraviolet)-C light with wavelengths between 200 and 230 nm is currently being considered for use in living spaces. UV-C light with wavelengths between 200 and 230 nm can provide a germicidal effect by deactivating viruses and killing germs. Furthermore, UV light with a wavelength between 200 and 230 nm has a low penetration depth in skin and eye tissue, thus preventing the light from harming people.

Furthermore, it is of interest to combine the advantageous properties of disinfection (bactericidal) lighting with desired properties of general lighting arrangements. It will be appreciated that important characteristics for many lighting arrangements are that they shall be arranged to provide uniform illumination. Another important aspect of lighting arrangements is the increasing need of providing energy efficiency during operation. Solid state light sources such as light emitting diodes, LEDs, for illumination purposes continues to attract attention by providing numerous advantages compared to incandescent lamps, fluorescent lamps, neon tube lamps, etc., such as a longer operational life, a reduced power consumption, and an increased efficiency related to the ratio between light energy and heat energy. However, as LEDs are point sources, there is a problem of producing LED based lighting arrangements providing uniform illumination.

EP3336417A1 discloses a lighting system that combines an arrangement of UV LEDs which face a light exit window and an arrangement of visible light LEDs which face a reflector arrangement. The reflection can be used to provide desired beam shaping or diffusion so that beam shaping components are not needed at the exit window.

U.S. Ser. No. 10/413,626B discloses a multiple light emitter device which inactivates microorganisms. The device includes a blue light emitter and a violet light emitter. A light converting material is arranged to convert at least a portion of light from the light emitters. Any unconverted light emitted from the light emitters and converted light emitted from the at least one light-converting material mixes to form a combined light, the combined light being white.

Hence, it is desired to provide lighting arrangements which may provide a desired lighting with respect to demands or requirements of illumination and/or energy efficiency, and which furthermore may provide a disinfection or bactericidal lighting effect during operation.

SUMMARY OF THE INVENTION

It is an object of the present invention to provide lighting arrangements which may provide a desired lighting with respect to demands or requirements of illumination and/or energy efficiency, and which furthermore may provide a disinfection or bactericidal lighting effect during operation.

This and other objects are achieved by providing a lighting arrangement having the features in the independent claim. Preferred embodiments are defined in the dependent claims.

Hence, according to the present invention, there is provided a lighting arrangement, comprising at least one first solid state light source arranged to emit visible light in a wavelength range from 430 to 800 nm, and at least one second solid state light source arranged to emit second light of at least one of violet light and ultraviolet (UV) light in a wavelength range from 315 to 420 nm. The lighting arrangement further comprises a reflector comprising at least one light-reflecting surface, wherein the reflector at least partially encloses the at least one first solid state light source and the at least one second solid state light source. At least part of the reflector defines a mixing chamber for mixing at least part of the visible light emitted from the at least one first solid state light source and at least part of the second light emitted from the at least one second solid state light source. The lighting arrangement further comprises a light exit window, wherein the visible light and the second light mixed by the mixing chamber are arranged to exit the lighting arrangement through the light exit window. The lighting arrangement further comprises at least one third solid state light source arranged to emit UV light in a wavelength range from 190 to 315 nm, wherein the at least one third solid state light source is arranged outside the mixing chamber.

The (spectral power distribution of the) at least one third solid state light source is different from the (spectral power distribution of the) at least second solid state light source.

Thus, the present invention is based on the idea of providing a combination of illumination and disinfection lighting by a lighting arrangement which is configured to emit visible light for illumination purposes and violet and/or UV light for disinfection purposes. By mixing visible light and violet and/or UV light in the mixing chamber for subsequent transmission through the light exit window, and emitting UV light from one or more positions outside the mixing chamber, the lighting arrangement may hereby meet requirements and/or desires of illumination whilst at the same time providing lighting with disinfectional or bactericidal effect.

The present invention is advantageous in that the lighting arrangement provides a spatial illumination and disinfection at high efficiency and/or low cost and/or long lifetime. The violet and/or UV light emitted from the second solid state light source(s) is optimally distributed and/or provided from the relatively large light exit window. In addition, the mixing chamber defined by at least part of the reflector is typically (more) susceptible for lower UV wavelengths, i.e. more susceptible for UV wavelengths that are lower than of the violet and/or UV light emitted from the second solid state light source(s), which may lead to degradation of materials used in the mixing chamber.

The present invention is advantageous in that the lighting arrangement, via its mixing chamber defined by at least part of the reflector, is able to achieve a very high degree of mixing of the light before exiting through the light exit window. More specifically, the light-reflective surface(s) of the reflector ensure that almost all of the light emitted towards the light-reflective surfaces will be reflected and eventually be coupled out from the light exit window.

The present invention is further advantageous by the possibility to provide different properties of the second solid state light source(s) with respect to the third solid state light source(s), in order to meet desirable effects of the disinfection lighting whilst at the same time providing a cost-efficient lighting arrangement. For example, the second solid state light source(s) may be relatively inexpensive and may have a relatively high efficiency, while the third solid state light source(s) may be relatively expensive and may have a relatively low efficiency.

The present invention is further advantageous in that the lighting arrangement may provide the violet and/or UV light according to a required and/or desired emission. For example, the lighting arrangement may be arranged to direct the violet and/or UV light to specific areas, e.g. in a room, where a disinfection effect is particularly desirable or required.

The present invention is further advantageous in that the ability of the lighting arrangement to provide mixed light of visible light and violet and/or UV light from the mixing chamber, and UV light from position(s) outside the mixing chamber achieves an aesthetically attractive lighting arrangement upon operation. Furthermore, an observer viewing the lighting arrangement may perceive the UV light from the position(s) outside the mixing chamber.

The present invention is further advantageous in that the lighting arrangement of the present invention comprises relatively few components. The low number of components is advantageous in that the lighting arrangement is relatively inexpensive to fabricate. Moreover, the low number of components of the lighting arrangement implies an easier recycling, especially compared to devices or arrangements comprising a relatively high number of components which impede an easy disassembling and/or recycling operation.

The lighting arrangement comprises at least one first solid state light source. By the term "solid state light source" (SSL source), it is here meant a light source which uses one or more semiconductor diodes. For example, the solid state light source may comprise light-emitting diodes, LEDs, organic light-emitting diodes, OLEDs, polymer light-emitting diodes, PLEDs, laser diodes, superluminescent diodes, etc., as sources of illumination. The first solid state light source is arranged to emit visible light. By the term "visible light", it is here meant light within a wavelength range of 430 to 800 nm which can be perceived by the human eye. The lighting arrangement further comprises at least one second solid state light source arranged to emit second light of at least one of violet light and ultraviolet, UV, light in a wavelength range from 315 to 420 nm. By the term "violet light", it is here meant light at the higher end of the visible spectrum, in a wavelength range of 380 to 450 nm, and by the term "ultraviolet light", it is here meant light in wavelength range of 100 to 400 nm. Hence, according to the present invention, the at least one second solid state light source arranged to emit second light of violet light and/or UV light in a wavelength range from 315 to 420 nm.

The lighting arrangement further comprises a reflector comprising at least one light-reflecting surface. By the term "reflector", it is here meant substantially any element, structure, device, or the like, which is configured to reflect incident light. The reflector at least partially encloses the at least one first solid state light source and the at least one second solid state light source. In other words, the first and second solid state light sources are at least partially surrounded by the reflector such that the reflector is arranged to reflect the incoming light from the first and second solid state light sources during operation. The reflector defines a mixing chamber for mixing at least part of the visible light emitted from the at least one first solid state light source. In other words, via the light-reflecting surface(s) of the reflector, the reflector is able to mix the light emitted from the first solid state light source(s) within the mixing chamber.

The lighting arrangement further comprises a light exit window. By the term "light exit window", it is here meant a material (e.g. glass) through which light may exit. The visible light and the violet and/or UV light mixed by the mixing chamber are arranged to exit the lighting arrangement through the light exit window. In other words, the exit window is arranged to couple out the mixed light.

The lighting arrangement further comprises at least one third solid state light source arranged to emit UV light in a wavelength range from 190 to 315 nm, wherein the at least one third solid state light source is arranged outside the mixing chamber. In other words, the third solid state light source(s) are provided on or in the lighting arrangement whilst not being arranged within the mixing chamber as defined by at least part of the reflector.

According to an embodiment of the present invention, the at least one third solid state light source may be arranged on a portion of the reflector. Hence, the third solid state light source(s) is (are) arranged on a portion or part of the reflector which does not define the mixing chamber, as the third solid state light source(s) is (are) arranged outside the mixing chamber.

According to an embodiment of the present invention, the at least one third solid state light source may be arranged to emit UV light in a wavelength range from 280 to 315 nm. Hence, the third solid state light source(s) may be arranged to emit ultraviolet B, UV-B, light.

According to an embodiment of the present invention, the at least one third solid state light source may be arranged to emit UV light in a wavelength range of 190 to 230 nm. As ultraviolet C, UV-C, light may be defined as light in the wavelength range of 100 to 280 nm, the third solid state light source(s) may hereby be arranged to emit light in a wavelength sub-range of the UV-C light. Alternatively, the at least one third solid state light source may be arranged to emit light in a wavelength range of 230 to 280 nm, which light may be labeled or characterized as "near UV-C light".

According to an embodiment of the present invention, the at least one third solid state light source may be arranged to emit violet light in a wavelength range from 190 to 230 nm. As violet light may be defined as light in the wavelength range of 100 to 280 nm, the third solid state light source(s) may hereby be arranged to emit light in a wavelength sub-range of the UV-C light.

According to an embodiment of the present invention, the light exit window may be a diffuser which has a reflectivity in the range from 30% to 80% for the visible light. By the term "diffuser", it is here meant substantially any element, material, etc., which is arranged to diffuse the light incident thereon. As the light exit window in the form of a diffuser has a reflectivity in the range from 30% to 80% for the visible light, it is partially reflective, i.e. semi-reflective. Hence, the light exit window according to the embodiment is advantageous in in that some of the light incident on the light exit window will be reflected back into the mixing chamber, leading to an even more improved light mixing within the mixing chamber before the visible light exits the lighting arrangement.

According to an embodiment of the present invention, the light exit window may comprise at least one optical element configured to diffract, refract and/or diffuse the visible light and the second light mixed by the mixing chamber. By the term "optical component", it is here meant substantially any component, element, or the like, which is configured or arranged to influence, guide and/or affect the light via diffraction, refraction and/or diffusion. The present embodiment is advantageous in that the optical component(s) is (are) able to affect the light coupled out from the exit window in order to meet the requirements and/or desires of the illumination and/or bactericidal lighting of the lighting arrangement.

According to an embodiment of the present invention, the at least one first solid state light source and the at least one second solid state light source may be arranged at a base portion of the reflector, wherein the base portion is arranged opposite the light exit window. The present embodiment is advantageous in that this position of the first and second solid state light sources may result in an even higher degree of mixing of the light within the mixing chamber before the light exits through the light exit window.

According to an embodiment of the present invention, a number of the at least one second solid state light source, $N_1$, and a number of the at least one third solid state light source, $N_2$, may fulfil $N_1 > 2 \cdot N_2$. Hence, the number of second solid state light sources, arranged within the mixing chamber, may be significantly larger than the number of third solid state light sources, arranged outside the mixing chamber.

According to an embodiment of the present invention, the at least one third solid state light source may comprise a plurality of light sources, wherein each third solid state light source may be arranged to emit light away from the light exit window, and wherein at least a first third solid state light source may be arranged to emit light in at least a first direction, and at least a second third solid state light source may be arranged to emit light in at least a second direction, wherein the at least one first direction is different from the at least one second direction. Hence, each third solid state light source of the plurality of third solid state light sources may be arranged to emit light in a respective direction away from the light exit window, i.e. in a direction such that light does not impinge on the light exit window. Furthermore, each third solid state light source of the plurality of third solid state light sources may be arranged to emit light in a unique, respective direction, such that two different light beams or light directions do not cross or intersect.

According to an embodiment of the present invention, the light exit window may be non-transmissive for the UV light emitted from the at least one third solid state light source. Hence, the light exit window may be arranged to block the UV light emitted from the third solid state light source(s).

The lighting arrangement further comprises a controller configured to individually control the at least one second solid state light source and the at least one third solid state light source. Hence, the controller may be configured to control the operation of each of the second solid state light source(s) and/or the third solid state light source(s). For example, the controller may be configured to control one or more properties, such as intensity or spectral power distribution, of the light emitted from the second and/or third solid state light sources. As a result, the relative amounts of light from the second solid state light source and the third solid state light source may be varied in order to change or further optimize the disinfection properties of the lighting arrangement, depending on, for example, the type of pathogen that is aimed to be inactivated.

According to an embodiment of the present invention, the at least one third solid state light source may be arranged on the light exit window.

According to an embodiment of the present invention, there is provided a lighting device comprising a lighting arrangement according to any one of the preceding embodiments. The lighting device further comprises a housing at least partially enclosing the lighting arrangement, wherein the at least one third solid state light source is arranged at least partially within the housing.

According to an embodiment of the present invention, the lighting device is one of a light emitting diode, LED, device and a LED tube, T-LED.

According to an embodiment of the present invention, there is provided a luminaire, comprising a lighting arrangement or a lighting device according to any one of the preceding embodiments. The luminaire further comprises an electrical connection connected to the lighting arrangement for a supply of power to the at least one first solid state light source, the at least one second solid state light source and the at least one third solid state light source of the lighting arrangement.

Further objectives of, features of, and advantages with, the present invention will become apparent when studying the following detailed disclosure, the drawings and the appended claims. Those skilled in the art will realize that different features of the present invention can be combined to create embodiments other than those described in the following.

BRIEF DESCRIPTION OF THE DRAWINGS

This and other aspects of the present invention will now be described in more detail, with reference to the appended drawings showing embodiment(s) of the invention.

DETAILED DESCRIPTION

Figure 1:
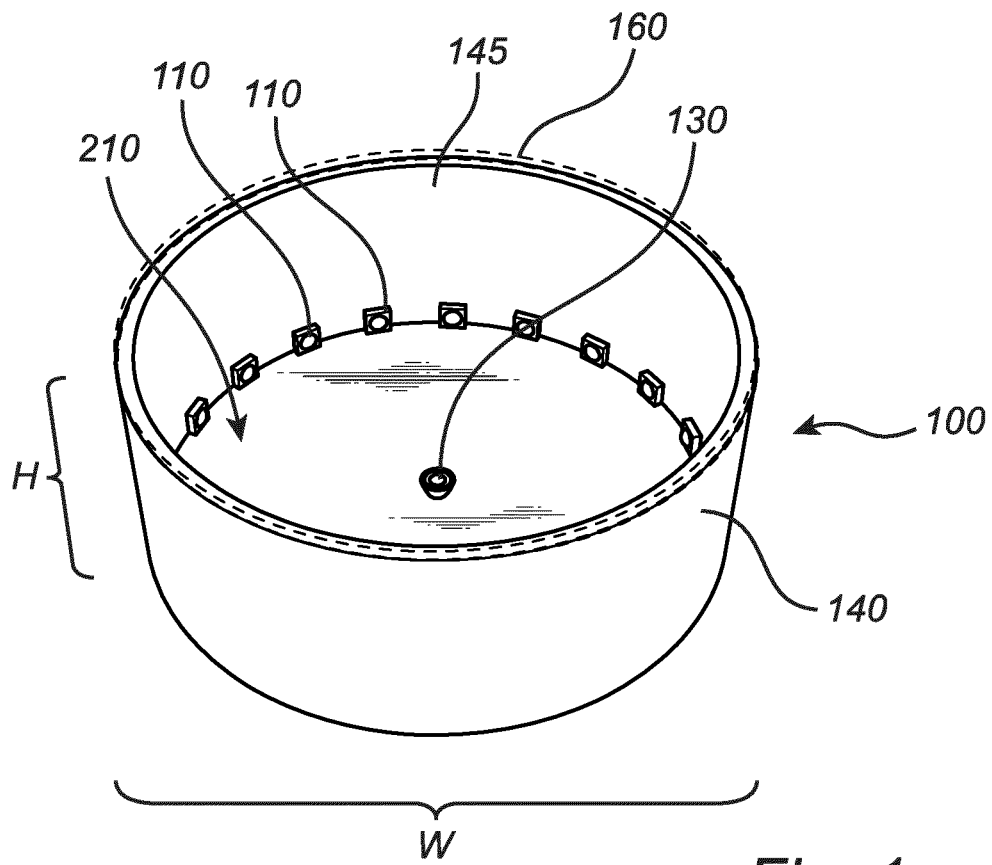
FIG. 1 schematically shows a lighting arrangement according to an exemplifying embodiment of the present invention, FIGS. 2 and 3 schematically show cross-sections of lighting arrangements according to exemplifying embodiments of the present invention, FIGS. 4*a* and 4*b* schematically shows lighting devices comprising a lighting arrangement according to exemplifying embodiments of the present invention, and FIG. 5 schematically shows a luminaire comprising a lighting arrangement according to exemplifying embodiments of the present invention.

FIG. 1 schematically shows a lighting arrangement 100 according to an exemplifying embodiment of the present invention. The lighting arrangement 100 comprises a plurality of first solid state light sources 110, which, for example, may comprise one or more light-emitting diodes, LEDs. The first solid state light sources 110 are arranged to emit visible light in a wavelength range from 430 to 800 nm. The visible light may be white light. The white light may have a color temperature, CT, in the range from 2000 to 6000 K. The white light may have a color rendering index, CRI, of at least 80. The CRI R9 of the white light may be >0. The white light may have a color point within 15 SDCM, like especially within 10 SDCM, like within 7 SDCM, from the black body locus, BBL. The first solid state light sources 110 may be one or more white solid state light sources such as one or more white LEDs.

In this example, a plurality of first solid state light sources 110 are shown, but it should be noted that the lighting arrangement 100 may comprise a single first solid state light source 110. Furthermore, the positioning of the first solid state light source(s) 110 in the lighting arrangement 100 may be different than that shown.

The lighting arrangement 100 further comprises a second solid state light source 130 arranged to emit violet light and/or UV light in a wavelength range from 315 to 420 nm. It should be noted that the mentioned wavelength range from 315 to 420 nm may comprise a first wavelength sub range of 315 to 380 nm (UV-A light) and a second wavelength sub range of 380 to 420 nm (violet light). In this example, the lighting arrangement 100 only comprises a single second solid state light source 130, but it should be noted that the lighting arrangement 100 may comprise an arbitrary number of second solid state light sources 130. The second solid state light source 130 may, for example, be a LED, a laser diode or a superluminescent diode.

The lighting arrangement 100 further comprises a reflector 140 which at least partially encloses the first and second solid state light sources 110, 130. The first and second solid state light sources 110, 130 are arranged at a base portion 210 of the reflector 140. The reflector 140 further comprises one or more light-reflecting surfaces 145. Here, the light-reflecting surface 145 is defined as a circumferential side wall, which, according to this example, has a circular cross-section taken in a plane parallel with the base portion 120. Hence, in this exemplifying embodiment of the lighting arrangement 100, the base portion 210 and the reflecting surface 125 of the reflector 140 define a cylinder shape of the reflector 140.

The lighting arrangement 100 further comprises a light exit window 160 arranged opposite the base portion 210 of the reflector 140. In FIG. 1, it should be noted that the light exit window 160 is merely indicated by a dashed line show in its outer contour for reasons of visibility of (other) parts and components of the lighting arrangement 100. The light exit window 160 may, for example, be a plate or a disk. The visible light emitted from the first solid state light sources 110 and the violet and/or UV light emitted from the second solid state light source 130 are arranged to be mixed in a mixing chamber 150 defined by at least a portion of the reflector 140 and arranged to exit the lighting arrangement 100 through the light exit window 160.

In the following, embodiments and examples of the mixing chamber 150 defined by at least a portion of the reflector 140 of the lighting arrangement 100 are provided, whereas further embodiments and examples of the lighting arrangement 100 are provided in FIGS. 2-4.

The mixing chamber 150 as defined by at least part of the reflector 140 of the lighting arrangement 100 as exemplified in FIG. 1 has a width, W, and a height, H. The height, H, of the mixing chamber 150 is defined as the height of the light-reflective surface 145 in the form of a circumferential side wall. This height, H, of the mixing chamber 150 for the embodiment shown in FIG. 1 may also be interpreted as the distance between the base portion 210 and the light exit window 160. The width, W, of the mixing chamber 150 is defined as having a base surface extension being the smallest distance between two opposite points on the periphery of the surface of the base portion 210. In the embodiment shown in FIG. 1, the width, W, of the mixing chamber 150 is the diameter of the base portion 120. An aspect ratio of the width, W, and the height, H, of the mixing chamber 150 within the range of 1 to 8 may increase the light mixing of the reflector 140 while the efficiency of the lighting arrangement 100 is not lowered beyond what is acceptable. Tests have been performed evaluating the efficiency and the uniformity of light coupled out from the lighting arrangement 100 depending on the aspect ratio. These tests have been performed with a mixing chamber 150 with a width, W, (i.e. diameter) of 150 mm, wherein the reflectivity of the light exit window 160 is kept at 50%, and wherein the height, H, of the mixing chamber 150 is varied between 10 mm and 50 mm. The first solid state light source 100 has been placed adjacent to the base portion 120. The tests show that the contrast, which is the ratio of the highest intensity and the lowest intensity of the light emitted from the lighting arrangement 100 is rapidly decreasing from 18 to 2 when the height, H, is increased from 10 mm to 20 mm (i.e. the aspect ratio is decreased from 15 to 7.5). When the height, H, is increased from 20 to 45, the contrast is decreased from 2.0 to 1.7. Moreover, the tests show that the efficiency decreases more or less linearly from 96.0% to 94.5% when the height, H, is increased from 15 mm to 50 mm.

According to the example of the lighting arrangement 100 in FIG. 1, the base portion 120 has a highly reflective inner surface, i.e. in the range of 90% to 100% for the visible light emitted by the first solid state light source 110. Moreover, the absorbance of the base portion 120 is close to zero for light emitted from the first solid state light source 110. It will be appreciated that an absorbance close to zero results in a high efficiency of the lighting arrangement 100. The base portion 120 may be made of metal or glass. The base portion 120 may for example be covered by a sheet of reflecting material or be painted with a coating reflector. The sheet of reflecting material may be a MCPET foil. The coating reflector may, for example, be $TiO_2$ powder particles mixed with clear silicone. Instead of $TiO_2$ powder, $Al_2O_3$ and/or $BaSO_4$ powder may be used and mixed with clear silicone.

The light-reflecting surface 145 has a highly reflective inner surface, i.e. in the range of 90% to 100% for the visible light emitted by the first solid state light source. Moreover, the absorbance of the light-reflecting surface 145 is close to zero for light emitted from the first solid state light source 110. It will be appreciated that an absorbance close to zero results in a high efficiency of the lighting arrangement 100.

The light-reflecting surface 145 may be covered by a sheet of reflecting material or may be painted with a coating reflector in the same way as the inner surface of the base portion 120. The base portion 120 and the light-reflecting surface 145 may be manufactured to be as white as possible, which may minimize light absorption in the mixing chamber 150.

The light exit window 160 of the lighting arrangement 100 is semi-reflective. More specifically, the reflectivity of the light exit window 160 is in the range of 30% to 80% for light emitted from the first solid state light source 110. The absorbance of the light exit window 160 is preferably less than 2% for light emitted from the first solid state light source 110. By having such a low absorbance in the light exit window 160 results in a high efficiency of the lighting arrangement 100. As a non-limiting example, the light exit window 160 may be made of Makrofol®. However, other material such as Lexan®, MB-grades, Lexalite Lumieo® and Flexi-Lume™ may also be used. It is also possible to use layers of scattering particles such as $TiO_x$ or $AlO_x$ in polymers such as silicone rubbers and adjust the reflectivity by the concentration of the particles and/or the thickness of the layer.

The light exit window 160 may comprise at least one optical element (not shown) configured to diffract, refract and/or diffuse the visible light emitted by the first solid state light source 110 and the second light emitted by the second solid state light source 130 mixed by the mixing chamber.

The light exit window 160 may further comprise luminescent material. The luminescent material may convert at least a part of light of a first color which impinges on the luminescent material of the light exit window 160 into light of a second color.

The first solid state light source(s) 110 of the lighting arrangement is (are) arranged to emit visible light in a wavelength range from 430 to 800 nm. For example, the one or more first solid state light sources 110 may be arranged to emit white light.

According to another example, one or more first solid state light sources 110 may be arranged to emit light of a specific color. For example, at least one of the first solid state light sources 110 may be arranged to emit red light, at least one of the first solid state light sources 110 may be arranged to emit green light and at least one of first solid state light sources 110 may be arranged to emit blue light. According to another example, the one or more first solid state light sources 110 may be arranged to emit blue light. In such a case, the light exit window 160 preferably comprises luminescent material converting a part of the blue light impinging on the luminescent material into light of another color.

Figure 2:
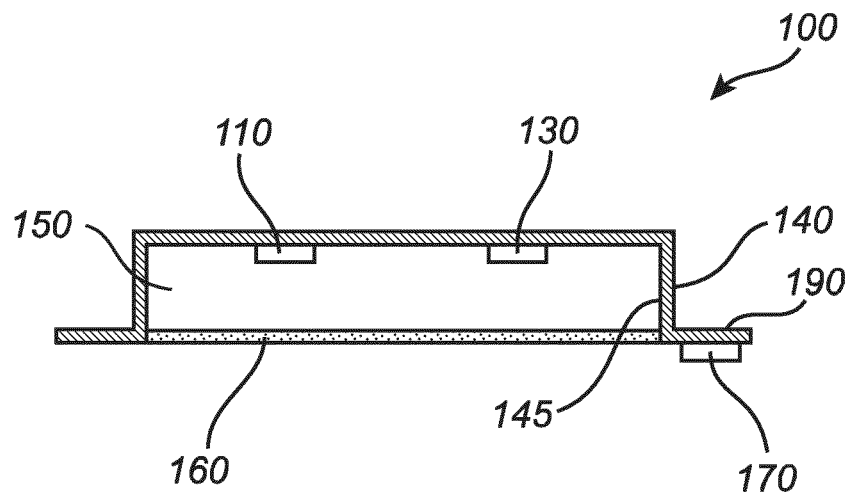

FIG. 2 schematically shows a cross-section of a lighting arrangement 100 according to an exemplifying embodiment of the present invention. It should be noted that the lighting arrangement 100 exemplified in FIG. 2 may constitute the lighting arrangement 100 exemplified in FIG. 1, and that it is referred to FIG. 1 and the associated text for an increased understanding of the features and/or components of the lighting arrangement 100 in FIG. 2. The lighting arrangement 100 comprises at least one first solid state light source 110 which is arranged to emit visible light in a wavelength range from 430 to 800 nm. The lighting arrangement 100 further comprises at least one second solid state light source 130 arranged to emit violet light and/or UV light in a wavelength range from 315 to 420 nm. Although the first and second solid state light sources 110, 130 are shown as single light sources, respectively, it will be appreciated that the number of first and second solid state light sources 110, 130 may be arbitrary.

The lighting arrangement 100 in FIG. 2 further comprises a reflector 140 comprising at least one light-reflecting surface 145, as previously described in relation to FIG. 1. The reflector 140 at least partially encloses the first and second solid state light sources 110, 130. The reflector 140 defines a mixing chamber 150 for mixing at least part of the visible light emitted from the at least one first solid state light source 110 and at least part of the second light (i.e. the violet and/or UV light) emitted from the at least one second solid state light source 130.

The lighting arrangement 100 in FIG. 2 further comprises a light exit window 160. The light mixed by the mixing chamber 150 is arranged to exit the lighting arrangement 100 through the light exit window 160.

The lighting arrangement 100 in FIG. 2 further comprises at least one third solid state light source 170 arranged to emit UV light in a wavelength range from 190 to 315 nm. Hence, the third solid state light source is arranged to emit UV-B and/or UV-C light in the wavelength range of 190 to 315 nm. In this example, the lighting arrangement 100 only comprises a single third solid state light source 170, but it should be noted that the lighting arrangement 100 may comprise an arbitrary number of third solid state light sources 170. For example, the number of the second solid state light sources 130, $N_1$, and the number of the third solid state light sources 170, $N_2$, may fulfil $N_1 > 2 \cdot N_2$, such as $N_1 > 3 \cdot N_2$ or $N_1 > 5 \cdot N_2$.

The third solid state light source 170 is arranged outside the mixing chamber 150 as defined by at least part of the reflector 140 of the lighting arrangement 100. In this example, the third solid state light source 170 is provided on a part or portion 190 of the reflector 140 which does not define the mixing chamber 150. Hence, the third solid state light source 170 is arranged on a part or portion 190 of the reflector 140 outside the mixing chamber 150. Thus, the light emitted from the third solid state light source 170 is not coupled out by the light exit window 160. Furthermore, the light emitted from the third solid state light source 170 is arranged to not impinge on the light exit window 160. Also, the light exit window 160 may be non-transmissive for the UV light emitted from the third solid state light source 170.

Figure 3:
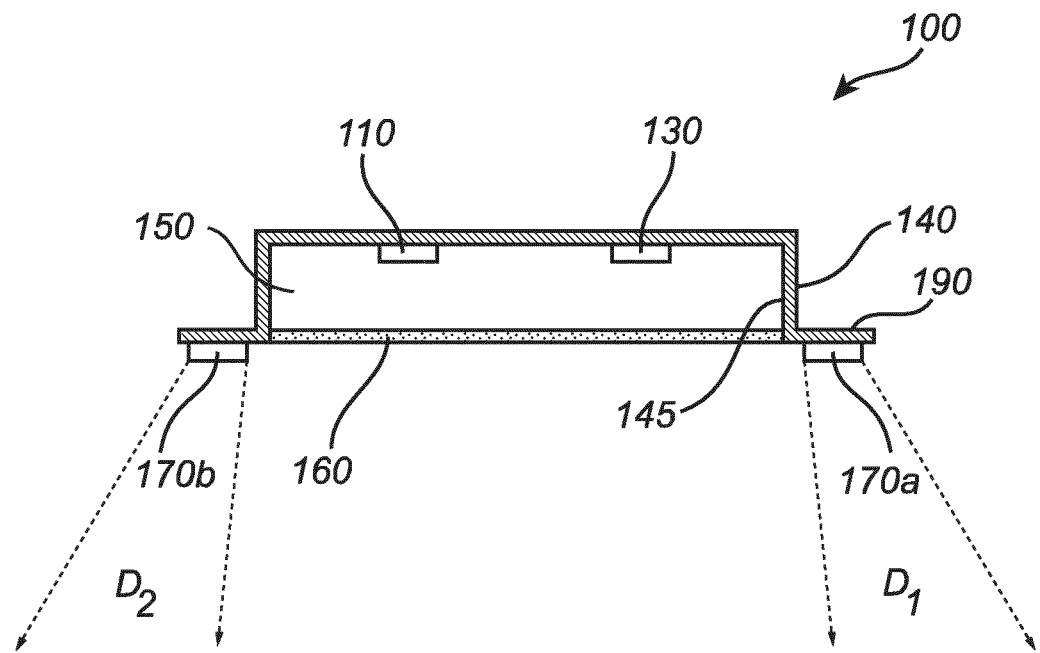

FIG. 3 schematically shows a cross-section of a lighting arrangement 100 according to an exemplifying embodiment of the present invention. It should be noted that the lighting arrangement 100 exemplified in FIG. 3 may constitute the lighting arrangement 100 exemplified in FIG. 1 or FIG. 2, and that it is referred to FIG. 1 and/or FIG. 2 and the associated text(s) for an increased understanding of the features and/or components of the lighting arrangement 100 in FIG. 3. In FIG. 3, the lighting arrangement comprises a first third light source 170a and a second third light source 170b, each arranged on a part or portion 190 of the reflector 140 outside the mixing chamber 150. It should be noted however, that the lighting arrangement 100 may comprise an arbitrary number of third solid state light sources. According to this example, each third solid state light source 170a, 170b may be arranged to emit light away from the light exit window 160, as indicated by the schematically indicated first and second (beam) directions, $D_1$, $D_2$, of the light emitted from the respective first and second third solid state light sources 170a, 170b. Furthermore, the first third solid state light source 170a may be arranged to emit light in the first direction, $D_1$, and the second third solid state light source 170b may be arranged to emit light in the second direction, $D_2$, wherein the first direction, $D_1$, is different from the second direction, $D_2$. Hence, the first and second third solid state light sources 170a, 170b may be arranged to emit light in a respective direction, $D_1$, $D_2$, away from the light exit window 160, i.e. in a direction such that light from each of the first and second third solid state light sources 170a, 170b does not impinge on the light exit window 160. Furthermore, the first and second third solid state light sources 170a, 170b may be arranged to emit light in a unique, respective direction, e.g. as indicated by the schematically indicated first and second (beam) directions, $D_1$, $D_2$, such that two different light beams or light directions do not cross or intersect.

Figures 4A, 4B:
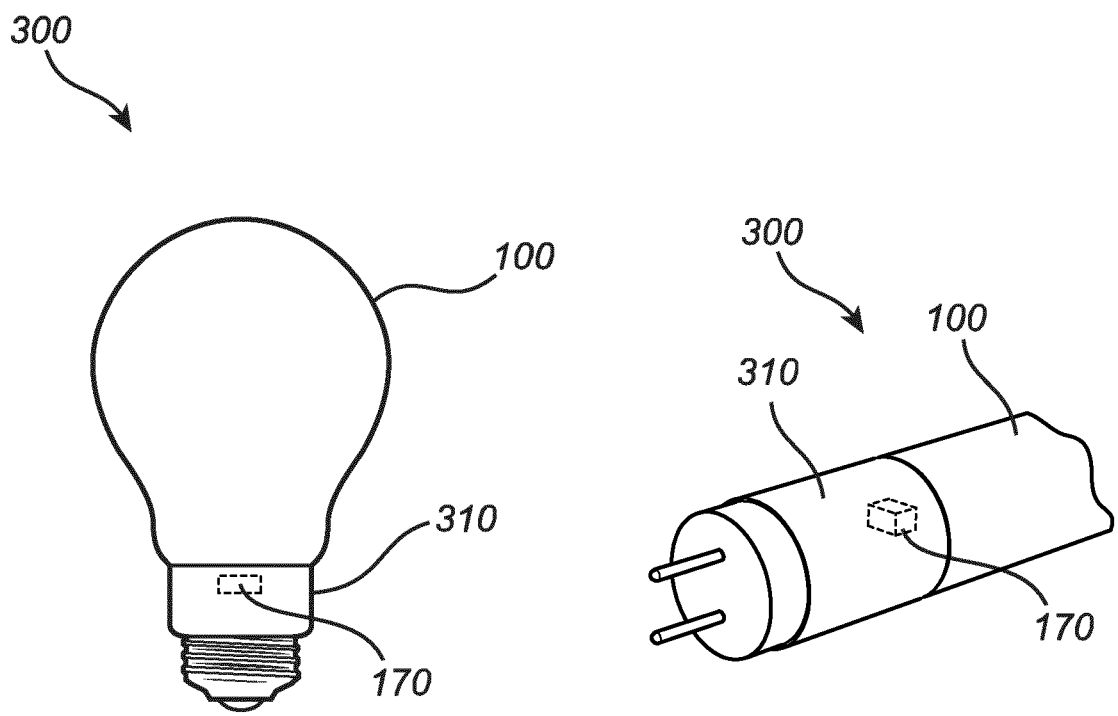

FIGS. 4a and 4b schematically show lighting devices 300 according to examples of the present invention. The lighting devices 300 each comprises a lighting arrangement 100 according to any one of the preceding embodiments, and further comprises a housing 310. It will be appreciated that the housings 310 may have different constructions or forms dependent on the kind of lighting device 300. The housing 310 at least partially encloses the lighting arrangement 100, wherein the at least one third solid state light source 170 is arranged at least partially within the housing 310. According to the example of the lighting device 300 in FIG. 4a, the lighting device 300 constitutes a LED device, such as a LED lamp. According to the example of the lighting device 300 in FIG. 4b, the lighting device 300 constitutes a LED tube, T-LED.

Figure 5:
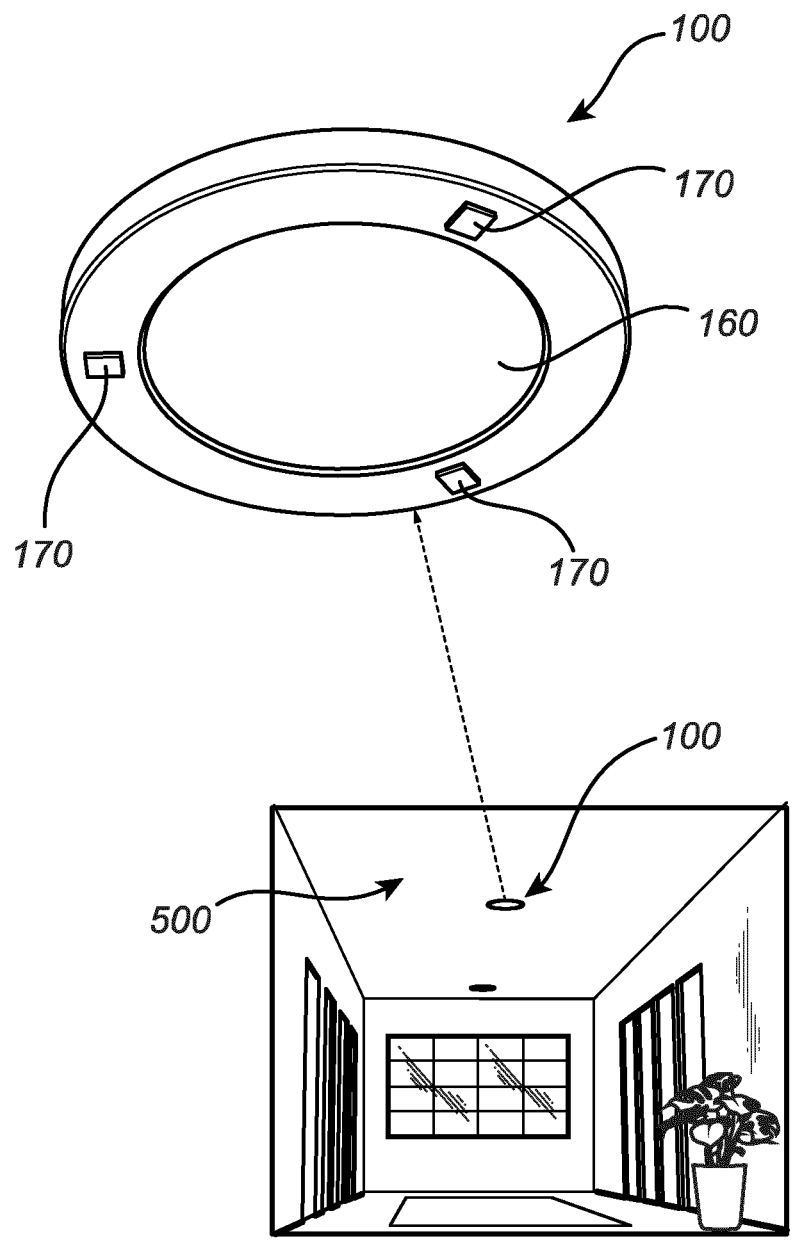

FIG. 5 schematically shows a luminaire 500 comprising one or more lighting arrangements 100 according to exemplifying embodiments of the present invention. For example, the luminaire 500 may be arranged in the ceiling of a corridor, a room, etc. It will be appreciated that the luminaire 500 may have different forms and/or constructions than those shown in FIG. 5, and that the luminaire 500 represents an example. The luminaire 500 comprises an electrical connection connected to the lighting arrangement 100 for a supply of power to the at least one first and second solid state light sources (not shown) and the third solid state light sources 170 of the lighting arrangement 100. The lighting arrangement 100 as exemplified comprises three third solid state light sources 170 arranged to emit UV light in a wavelength range from 190 to 315 nm. It should be noted that one or more of the third solid state light sources 170 may be arranged on the light exit window 160 (not shown). The first solid state light source(s) arranged to emit visible light in a wavelength range from 430 to 800 nm, and the second solid state light source(s) arranged to emit second light of at least one of violet light and ultraviolet, UV, light in a wavelength range from 315 to 420 nm, are provided behind the light exit window 160, and therefore not shown in FIG. 5.

It will be appreciated that the wavelength range of the UV light may be defined in a range from 100 to 380 nm and can be divided into different types of UV light/UV wavelength ranges (Table 1). Different UV wavelengths of radiation may have different properties and thus may have different compatibility with human presence and may have different effects when used for disinfection (Table 1).

TABLE 1

Properties of different types of UV wavelength light

| Name | Short name | Wavelength (nm) | (Relative) sterilization effectiveness Bacteria | (Relative) sterilization effectiveness Viruses | Safe Radiation | Vitamin D generation | Ozone generation |
|---|---|---|---|---|---|---|---|
| Violet | V | 380-420 | +/− | − | + | | |
| Ultra-violet A | UV-A | 315-380 | + | − | + | | |
| Ultra-violet B | UV-B | 280-315 | + | +/− | +/− | + | |
| Near ultra-violet C | Near UV-C | 230-280 | + | + | − | | |
| Far ultra-violet | Far UV | 190-230 | + | + | + | | +/− |
| Extreme ultra-violet C | Extreme UV-C | 100-190 | + | + | − | | + |

It should be noted that each UV type/wavelength range may have different benefits and/or drawbacks. Relevant aspects may be (relative) sterilization effectiveness, safety (regarding radiation), and ozone production (as result of its radiation). Depending on an application a specific type of UV light or a specific combination of UV light types may be selected and provides superior performance over other types of UV light. UV-A may be (relatively) safe and may kill bacteria, but may be less effective in killing viruses. UV-B may be (relatively) safe when a low dose (i.e. low exposure time and/or low intensity) is used, may kill bacteria, and may be moderately effective in killing viruses. UV-B may also have the additional benefit that it can be used effectively in the production of vitamin D in a skin of a person or animal. Near UV-C may be relatively unsafe, but may effectively kill bacteria and viruses. Far UV may also be effective in killing bacteria and viruses, but may be (relatively to other UV-C wavelength ranges) (rather) safe. Far-UV light may generate some ozone which may be harmful for human beings and animals. Extreme UV-C may also be effective in killing bacteria and viruses, but may be relatively unsafe. Extreme UV-C may generate ozone which may be undesired when exposed to human beings or animals. In some application ozone may be desired and may contribute to disinfection, but then its shielding from humans and animals may be desired. Hence, in the table "+" for ozone production especially implies that ozone is produced which may be useful for disinfection applications, but may be harmful for humans/animals when they are exposed to it. Hence, in many applications this "+" may actually be undesired while in others, it may be desired.

The person skilled in the art realizes that the present invention by no means is limited to the preferred embodiments described above. On the contrary, many modifications and variations are possible within the scope of the appended claims. For example, one or more of the first, second and/or third solid state light sources 110, 130, 170, the reflector 140, etc., may have different shapes, dimensions and/or sizes than those depicted/described.

The invention claimed is:

1. A lighting arrangement, comprising:
   at least one first solid state light source arranged to emit visible light in a wavelength range from 430 to 800 nm,
   at least one second solid state light source arranged to emit second light of at least one of violet light and ultraviolet (UV) light in a wavelength range from 315 to 420 nm,
   a reflector comprising at least one light-reflecting surface, wherein the reflector at least partially encloses the at least one first solid state light source and the at least one second solid state light source, and wherein at least part of the reflector defines a mixing chamber for mixing at least part of the visible light emitted from the at least one first solid state light source and at least part of the second light emitted from the at least one second solid state light source,
a light exit window, wherein the visible light and the second light mixed by the mixing chamber are arranged to exit the lighting arrangement through the light exit window,
at least one third solid state light source arranged to emit UV light in a wavelength range from 190 to 315 nm, wherein the at least one third solid state light source is arranged outside the mixing chamber, and the at least one third solid state light source is arranged on the light exit window,
a controller configured to individually control the at least one second solid state light source and the at least one third solid state light source, and
the controller further being configured to control one or more properties of the light emitted from the second solid state light source and/or the third solid state light source.

2. The lighting arrangement according to claim 1, wherein the at least one third solid state light source is arranged on a portion of the reflector.

3. The lighting arrangement according to claim 1, wherein the at least one third solid state light source is arranged to emit UV light in a wavelength range from 280 to 315 nm.

4. The lighting arrangement according to claim 1, wherein the at least one third solid state light source is arranged to emit UV light in a wavelength range from 190 to 230 nm.

5. The lighting arrangement according to claim 1, wherein the light exit window is a diffuser which has a reflectivity in the range from 30% to 80% for the visible light.

6. The lighting arrangement according to claim 1, wherein the light exit window comprises at least one optical element configured to diffract, refract and/or diffuse the visible light and the second light mixed by the mixing chamber.

7. The lighting arrangement according to claim 1, wherein at least one of the at least one first solid state light source and the at least one second solid state light source are arranged at a base portion of the reflector, wherein the base portion is arranged opposite the light exit window.

8. The lighting arrangement according to claim 1, wherein a number of the at least one second solid state light source, $N_1$, and a number of the at least one third solid state light source, $N_2$, fulfil $N_1 > 2 \cdot N_2$.

9. The lighting arrangement according to claim 1, wherein the at least one third solid state light source comprises a plurality of light sources, wherein each third solid state light source is arranged to emit light away from the light exit window, and wherein at least a first third solid state light source is arranged to emit light in at least a first direction, and at least a second third solid state light source is arranged to emit light in at least a second direction, wherein the at least one first direction is different from the at least one second direction.

10. The lighting arrangement according to claim 1, wherein the light exit window is non-transmissive for the ultraviolet light emitted from the at least one third solid state light source.

11. A lighting device, comprising:
a lighting arrangement according to claim 1,
a housing at least partially enclosing the lighting arrangement,
wherein the at least one third solid state light source is arranged at least partially within the housing.

12. The lighting device according to claim 11, wherein the lighting device is one of a light emitting diode, LED, device and a LED tube, T-LED.

13. A luminaire, comprising:
at least one of the lighting arrangement according to claim 1, and
an electrical connection connected to the lighting arrangement for a supply of power to the at least one first solid state light source, the at least one second solid state light source, and the at least one third solid state light source.

14. A lighting arrangement, comprising:
at least one first solid state light source arranged to emit visible light in a wavelength range from 430 to 800 nm,
at least one second solid state light source arranged to emit second light of at least one of violet light and ultraviolet (UV) light in a wavelength range from 315 to 420 nm,
a reflector comprising at least one light-reflecting surface, wherein the reflector at least partially encloses the at least one first solid state light source and the at least one second solid state light source, and wherein at least part of the reflector defines a mixing chamber for mixing at least part of the visible light emitted from the at least one first solid state light source and at least part of the second light emitted from the at least one second solid state light source,
a light exit window, wherein the visible light and the second light mixed by the mixing chamber are arranged to exit the lighting arrangement through the light exit window,
at least one third solid state light source arranged to emit UV light in a wavelength range from 190 to 315 nm, wherein the at least one third solid state light source is arranged outside the mixing chamber,
a controller configured to individually control the at least one second solid state light source and the at least one third solid state light source, and
the controller further being configured to control one or more properties of the light emitted from the second solid state light source and/or the third solid state light source,
wherein the at least one third solid state light source comprises a plurality of light sources, wherein each third solid state light source is arranged to emit light away from the light exit window, and wherein at least a first third solid state light source is arranged to emit light in at least a first direction, and at least a second third solid state light source is arranged to emit light in at least a second direction, wherein the at least one first direction is different from the at least one second direction.

* * * * *